United States Patent
Koren et al.

(10) Patent No.: US 9,418,413 B1
(45) Date of Patent: Aug. 16, 2016

(54) SYSTEM AND A METHOD FOR AUTOMATIC RECIPE VALIDATION AND SELECTION

(75) Inventors: Shimon Koren, Haifa (IL); Or Shur, Nesher (IL)

(73) Assignee: CAMTEK LTD., Migdal Haemek (IL)

( * ) Notice: Subject to any disclaimer, the term of this patent is extended or adjusted under 35 U.S.C. 154(b) by 907 days.

(21) Appl. No.: 12/830,366

(22) Filed: Jul. 5, 2010

Related U.S. Application Data

(60) Provisional application No. 61/223,075, filed on Jul. 6, 2009.

(51) Int. Cl.
*G06T 7/00* (2006.01)
*G01N 21/95* (2006.01)

(52) U.S. Cl.
CPC ............ *G06T 7/001* (2013.01); *G01N 21/9501* (2013.01); *G06T 7/0004* (2013.01); *G06T 7/0006* (2013.01); *G06T 2207/30148* (2013.01)

(58) Field of Classification Search
None
See application file for complete search history.

(56) References Cited

U.S. PATENT DOCUMENTS

| | | | | |
|---|---|---|---|---|
| 5,544,256 | A * | 8/1996 | Brecher et al. | 382/149 |
| 6,330,354 | B1 * | 12/2001 | Companion et al. | 382/150 |
| 6,691,052 | B1 * | 2/2004 | Maurer | 702/81 |
| 6,826,298 | B1 * | 11/2004 | O'Dell et al. | 382/149 |
| 7,023,541 | B2 * | 4/2006 | Mizuo et al. | 356/237.4 |
| 7,283,882 | B1 | 10/2007 | Bransky et al. | |
| 7,383,156 | B2 | 6/2008 | Miyakawa et al. | |
| 8,290,241 | B2 | 10/2012 | Ono et al. | |
| 2005/0254045 | A1 | 11/2005 | Weiss | |
| 2006/0199287 | A1 * | 9/2006 | Fu | G01N 21/9501 438/16 |
| 2008/0226153 | A1 * | 9/2008 | Ono et al. | 382/141 |
| 2009/0226075 | A1 * | 9/2009 | Hiroi et al. | 382/149 |
| 2010/0119144 | A1 * | 5/2010 | Kulkarni et al. | 382/149 |
| 2010/0172570 | A1 * | 7/2010 | Sakai et al. | 382/151 |
| 2011/0164129 | A1 | 7/2011 | Regensburger | |

FOREIGN PATENT DOCUMENTS

| | | |
|---|---|---|
| TW | 200512794 | 4/2005 |
| TW | I244359 | 11/2005 |

OTHER PUBLICATIONS

Merriam Webster's Collegiate Dictionary, Tenth Edition, definition of "distance", 1997.*

* cited by examiner

*Primary Examiner* — Allen Chein

(74) *Attorney, Agent, or Firm* — Reches Patents

(57) ABSTRACT

A system, a non-transitory computer program product and a method for selecting an inspection recipe, the method includes: (i) obtaining an image of a structural element of the semiconductor device; (ii) calculating multiple types of distances between the image of the structural element and each of a plurality of reference images obtained by applying a plurality of inspection recipes; and (iii) automatically selecting at least one selected inspection recipe out of the plurality of inspection recipes based on values of the multiple types of distances.

19 Claims, 4 Drawing Sheets

400

SYSTEM AND A METHOD FOR AUTOMATIC RECIPE VALIDATION AND SELECTION

RELATED APPLICATIONS

This application claims the priority of U.S. provisional patent Ser. No. 61/223,075 and filing date Jul. 6, 2009, which is incorporated herein by reference by its entirety.

BACKGROUND OF THE INVENTION

Wafer defect inspection is a common practice in the semiconductor manufacturing industry as a part of complicated yield analysis and control process. Although every automatic defect detection tool vendor utilizes different inspection principles and methods, all have one concept in common—the inspection recipe (also referred to as an inspection job). The mentioned inspection recipe is created with respect to some kind of representing wafer and is used for every wafer of the same origin (product, process etc.). All wafer inspection tools share the same "setup"→"run" scenario.

Most of the automatic inspection tools face the very same challenges of being invariant to process variation. That means that the same inspection recipe created using one representing wafer is being successfully used for the entire batch of wafers of the same kind.

SUMMARY OF THE INVENTION

A method for selecting an inspection recipe, the method may include according to an embodiment of the invention: obtaining an image of a structural element of the semiconductor device; calculating multiple types of distances between the image of the structural element and each of a plurality of reference images obtained by applying a plurality of inspection recipes; and automatically selecting at least one selected inspection recipe out of the plurality of inspection recipes based on values of the multiple types of distances.

The method may include calculating multiple types of distances, at least three distances or a majority of distances out of: (i) a difference between gray level histograms, (ii) a rectilinear (L1) distance, (iii) Euclidian (L2) length, (iv) Chi-square distance, (v) Bhattacharyya distance, (vi) Wasserstein metric, (vii) Swain metric, and (viii) normalized correlation.

The method may include generating a match value for each reference image based on values of the multiple types of distances between the image of the structural element and the reference image; and selecting each inspection recipe associated with a reference image that has a match value within an allowable match value range.

The method may include selecting multiple selected inspection recipes.

The method may include changing the type of distances to be calculated based on evaluation results obtained by applying the at least one selected inspection recipe.

The structural elements may be coated by a coating material that changes an optical property over time, wherein the plurality of inspection recipes differ from each other by a value of optical property of the coating material they are tuned to.

An inspection system may be provided. According to an embodiment of the invention the system may include: an image obtaining module for obtaining an image of a structural element of the semiconductor device; a distance calculator for calculating multiple types of distances between the image of the structural element and each of a plurality of reference images obtained by applying a plurality of inspection recipes; a selecting module for automatically selecting at least one selected inspection recipe out of the plurality of inspection recipes based on values of the multiple types of distances; and a controller for controlling the image obtaining module to apply each of the at least one selected inspection recipe.

The distance calculator may be adapted to calculate multiple types of distances, at least three distances or a majority of distances out of: (i) a difference between gray level histograms, (ii) a rectilinear (L1) distance, (iii) Euclidian (L2) length, (iv) Chi-square distance, (v) Bhattacharyya distance, (vi) Wasserstein metric, (vii) Swain metric, and (viii) normalized correlation.

The distance calculator may be adapted to generate a match value for each reference image based on values of the multiple types of distances between the image of the structural element and the reference image; and selecting each inspection recipe associated with a reference image that has a match value within an allowable match value range.

The selecting module may be adapted to select multiple selected inspection recipes.

The distance calculator may be adapted to change the type of distances to be calculated based on evaluation results obtained by applying the at least one selected inspection recipe.

The structural elements may are coated by a coating material that changes an optical property over time, wherein the plurality of inspection recipes may differ from each other by a value of optical property of the coating material they are tuned to.

A computer program product is provided. It may include, according to an embodiment of the invention, a non-transient computer readable medium that stores instructions for: obtaining an image of a structural element of the semiconductor device; calculating multiple types of distances between the image of the structural element and each of a plurality of reference images obtained by applying a plurality of inspection recipes; and automatically selecting at least one selected inspection recipe out of the plurality of inspection recipes based on values of the multiple types of distances.

The computer program product may store instructions for calculating multiple types of distances, a majority of distances or at least three distances out of: (i) a difference between gray level histograms, (ii) a rectilinear (L1) distance, (iii) Euclidian (L2) length, (iv) Chi-square distance, (v) Bhattacharyya distance, (vi) Wasserstein metric, (vii) Swain metric, and (viii) normalized correlation.

The computer program product may store instructions for generating a match value for each reference image based on values of the multiple types of distances between the image of the structural element and the reference image; and selecting each inspection recipe associated with a reference image that has a match value within an allowable match value range.

The computer program product may store instructions for selecting multiple selected inspection recipes.

The computer program product may store instructions for changing the type of distances to be calculated based on evaluation results obtained by applying the at least one selected inspection recipe.

The structural elements may be coated by a coating material that changes an optical property over time, wherein the plurality of inspection recipes may differ from each other by a value of optical property of the coating material they are tuned to.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

DETAILED DESCRIPTION OF THE DRAWINGS

Figure 1:
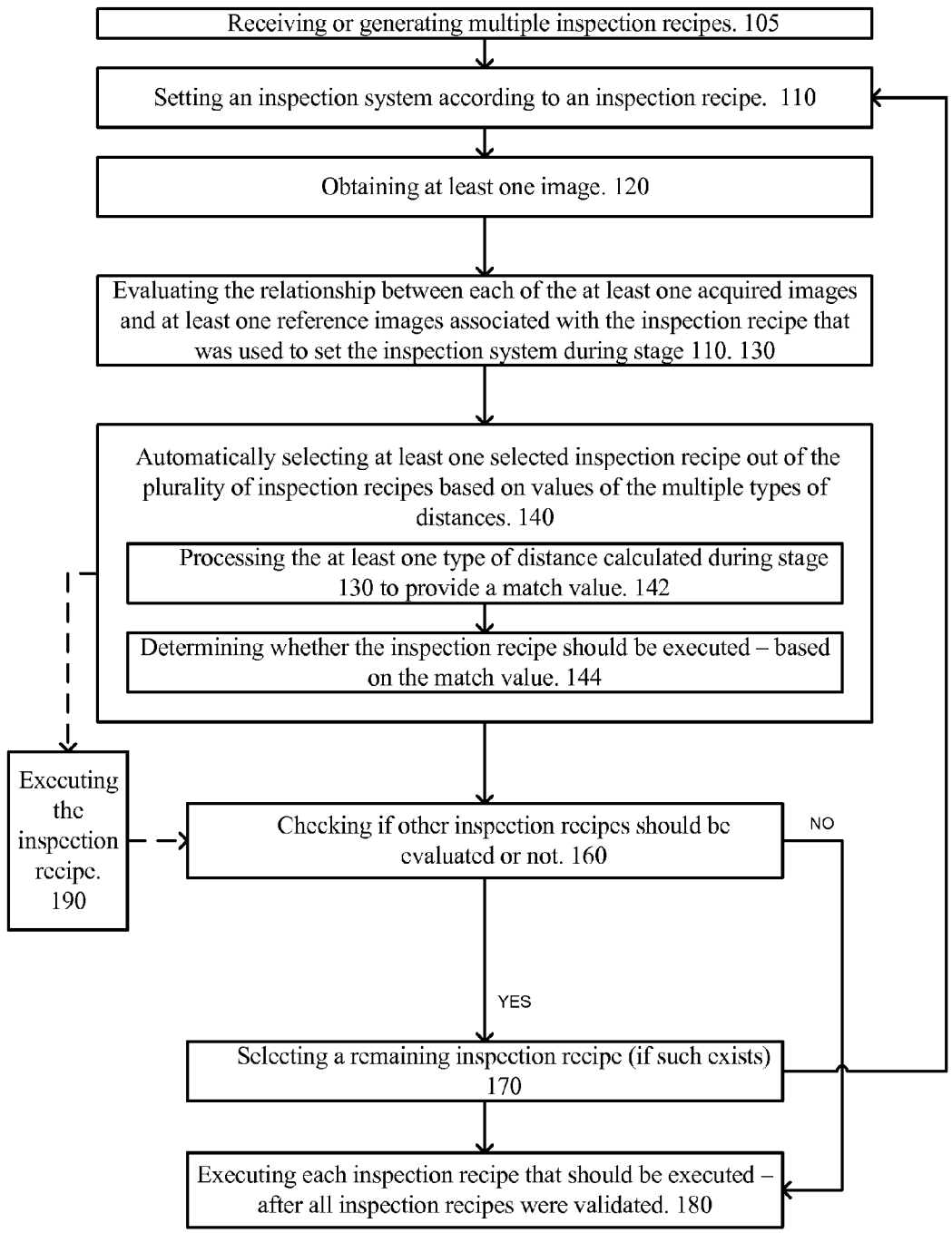
FIG. 1 illustrates a method according to an embodiment of the invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The following method, system and computer program product provide a robust and deterministic solution to at least one known type of process variation—global contrast and/or texture and/or reflectance change of the inspected targets on the wafer. The described kind of process variation is commonly encountered at wafer coating "aging" process (the phenomena when a coating liquid changes its optical properties between a first wafer in a batch to the last wafer in the batch).

The wafer coating process can be executed by dipping a wafer in a coating liquid as a part of an electroplating process. The coating liquid can change its optical characteristics (reflection, transparency, absorption) over time—resulting in relatively large changes in the acquired image. Thus, the acquired images of ideally identical structural elements can substantially differ from each other.

The method, system and computer program product provide recipe run-time adaptation and allow robust and reliable recipe selection/validation with respect to currently executed wafer, based on the pre-set criteria. They include executing only "good" inspection recipes out of the stored pool of existing trained inspection recipes.

The method, system and computer program product may select between a number of pre-defined (such as trained) inspection recipes, each one optimized for certain conditions of the wafer. These conditional can be a global reflection of the wafer, contrast values, optical characteristics of a coating liquid and the like.

Each inspection recipe may be optimized to detect defects of a typical image of a wafer related to previously mentioned state of process variation. The inspection system may browse through the mentioned inspection recipes, qualifies it using a combination of various statistical methods versus pre-stored optic metric and decides either to execute or not with respect to minimal match score.

The described comparison and matching technique (unlike other commonly used in the industry) does not base its decision on image features or image specific gray level. The robustness is achieved by a mentioned dedicated combination of statistical image analysis—stored wafer image reference versus run-time wafer image.

FIG. 1 illustrates a method 100 according to an embodiment of the invention.

Method 100 starts by stage 105 or receiving or generating multiple inspection recipes.

Stage 105 is followed by stage 110 of setting an inspection system according to an inspection recipe. Stage 110 may include applying a user defined optics state—including but not limited to illumination intensity, illumination type, collection set up, and magnification. Stage 110 may include applying recipe's saved image acquisition state.

Stage 110 is followed by stage 120 of obtaining at least one image. An image that is obtained during stage 120 can be referred to as an acquired image. Stage 120 may include obtaining a sequence of acquired images of the same structural reference (or area) or of different structural elements (or areas) of the wafer.

Stage 120 is followed by stage 130 of evaluating the relationship between each of the at least one acquired images and at least one reference images associated with the inspection recipe that was used to set the inspection system during stage 110. The evaluation is responsive to at least one predefined match criterion.

Stage 130 may be followed by stage 140 of automatically selecting at least one selected inspection recipe out of the plurality of inspection recipes based on values of the multiple types of distances. The evaluation is responsive to at least one predefined match criterion.

Stage 130 may include comparing at least one acquired image to at least one corresponding reference image.

Stage 130 may include calculating at least one type of distance between a pair of acquired image and reference image. The reference image of each pair is associated with the currently evaluated inspection recipe—the inspection recipe that was used to set the inspection system during stage 110. The calculating may include performing at least one statistical analysis of pixel values of each pair of acquired image and reference image.

Stage 130 may include using the following algorithms: Simplistic gray level histogram mean, L1 or L2 distribution; Chi-Square distribution; Bhattacharyya distance; Earth-mover's distance (a.k.a. Wassersstein metric); Swain metric; and Normalized correlation.

Stage 130 is followed by stage 140 of processing the at least one type of distance calculated during stage 130 to provide a match value. The processing may include applying statistical algorithms such as mean, variance, majority weighted sum and the like.

Stage 140 is followed by stage 150 of determining whether the inspection recipe should be executed—based on the match value. The value score can be compared to a match value minimum, match value maximum or to a match value range associated with the currently evaluated inspection recipe.

Stage 150 may be followed by: (i) stage 160 of checking if other inspection recipes should be evaluated or not, (ii) stage 170 of selecting a remaining inspection recipe (if such exists) and jumping to stage 110, and (iii) stage 180 of executing each inspection recipe that should be executed—after all inspection recipes were validated.

Alternatively, if stage 150 determines to that the inspection recipe should be executed then stage 150 may be followed by stage 190 of executing the inspection recipe. Stage 190 can be followed by a sequence of stages that may include stages 160 and 170.

The repetition of the various stages of method 100 may result in: (i) calculating multiple types of distances between an acquired image of a structural element of the wafer and each of a plurality of reference images obtained by applying a plurality of inspection recipes; and (ii) automatically selecting at least one selected inspection recipe out of the plurality of inspection recipes based on values of the multiple types of distances.

Figure 2:
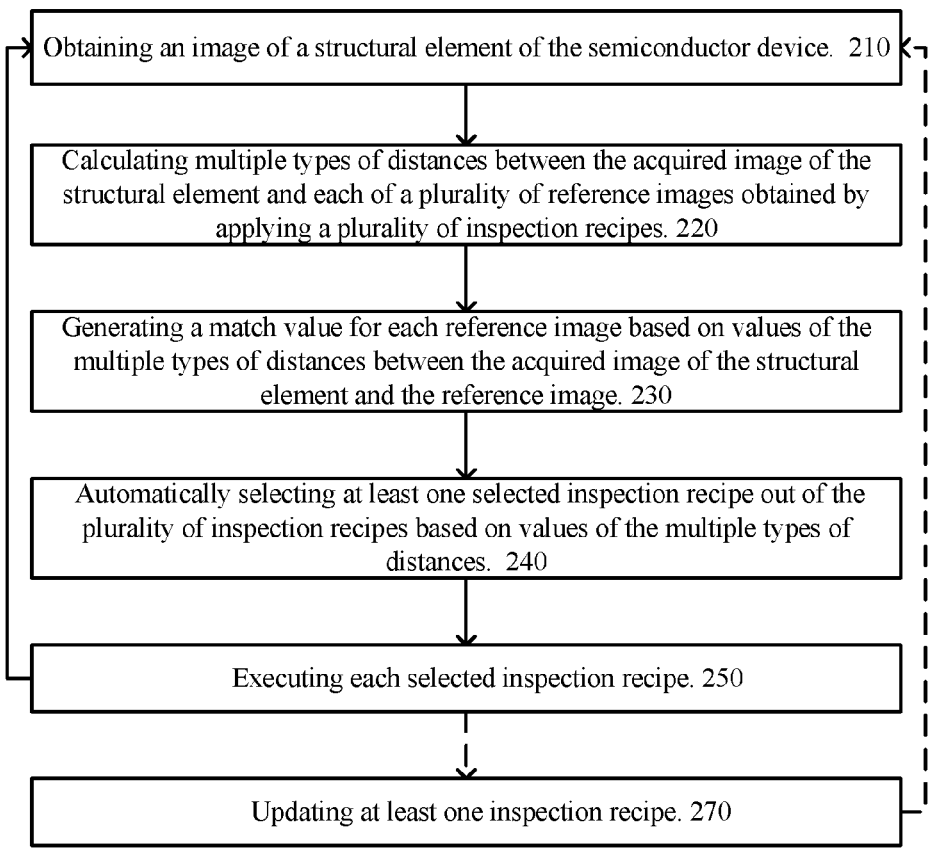
FIG. 2 illustrates a method according to an embodiment of the invention.

FIG. 2 illustrates method 200 according to an embodiment of the invention.

Method 200 includes:

i. Stage 210 of obtaining an image of a structural element of the semiconductor device. The structural element can be a bump, a trench, and the like.

ii. Stage 220 of calculating multiple types of distances between the acquired image of the structural element and each of a plurality of reference images obtained by applying a plurality of inspection recipes.

iii. Stage 230 of generating a match value for each reference image based on values of the multiple types of distances between the acquired image of the structural element and the reference image. The structural elements that are imaged may be coated by a coating material that changes an optical property over time and the plurality of inspection recipes may differ from each other by a value of optical property of the coating material they are tuned to.

iv. Stage 240 of automatically selecting at least one selected inspection recipe out of the plurality of inspection recipes based on values of the multiple types of distances. Stage 240 can be responsive to the match value of each pair of reference image and inspected image; and v. Stage 250 of executing each selected inspection recipe.

Stage 220 may include: (a) calculating multiple types of distances, (b) calculating a majority of multiple types of distances, or (c) calculating at least three types of distances out of:

(i) A difference between gray level histograms,
(ii) A rectilinear (L1) distance,
(iii) Euclidian (L2) length,
(iv) Chi-square distance,
(v) Bhattacharyya distance,
(vi) Wasserstein metric,
(vii) Swain metric, and
(viii) A normalized correlation.

Using multiple types of distances can assist in providing a robust selection of an inspected recipe. The robustness can be contributed to the different responses of the different types of distances to different types of changes such as process variations, changes in the reflectivity of a coating material and the like. It is noted that other types of distances may be calculated.

Stage 240 can include selecting each inspection recipe associated with a reference image that has a match value within an allowable match value range. The allowable match value range is determined in advance and may be determined by an operator (or other authorized person).

Stage 240 may include selecting multiple selected inspection recipes. Each of these selected inspection recipes should be executed during stage 250.

After executing one or more iterations of stages 210-260, method 200 can proceed by stage 270 of updating at least one inspection recipe.

Stage 270 may include changing the type of distances to be calculated based on evaluation results obtained by applying the at least one selected inspection recipe. Stage 270 can include omitting a previously selected type of distance if that type of distance did not contribute to the selection of the selected inspection recipe (if, for example there was a very low correlation between a value of that type of distance and a decision whether to select an associated inspection recipes). Stage 270 can include adding a new type of distance to be calculated during the next iterations of method 200. Stage 270 may be followed by stage 210.

Each method out of method 100 and 200 can include a stage of receiving instructions from an operator of the inspection system (or from any other authorized person). These instructions may determine the context of each inspection recipe, may determine which types of distances to calculate, how to calculate the match score and how to select an inspection recipes based on the match score. An instruction can limit the number of selected inspection recipes and can select which structural elements to image during the generation of the reference images and of the obtained images.

Figure 3:
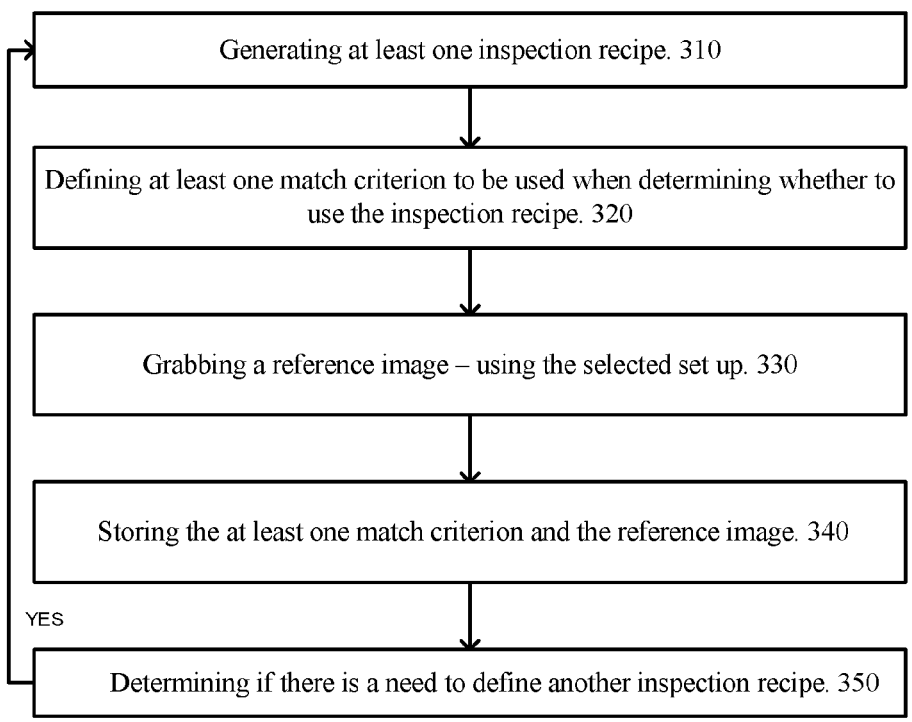
FIG. 3 illustrates a method according to an embodiment of the invention.

FIG. 3 illustrates a stage 105, according to an embodiment of the invention.

Stage 105 starts by stage 310 of generating at least one inspection recipe.

Stage 310 may include defining a set up (a state) for image acquisition (e.g. selecting optical characteristic for image acquisition, location on a wafer or other validated object, and so forth.

Stage 310 is followed by stage 320 of defining at least one match criterion to be used when determining whether to use the inspection recipe. The match criterion may include the types (or type) of distances to be calculated between an acquired image and a reference image, the manner in which the values of the one or more types of distances are to be processed to provide a match value and values of the match value that will result in selecting the inspection recipe or rejecting it.

Stage 330 is followed by stage 330 of grabbing a reference image—using the selected set up.

Stage 330 is followed by stage 340 of storing the at least one match criterion and the reference image.

Stage 310 may be followed by stage 350 of determining if there is a need to define another inspection recipe. If the answer is positive then stage 350 is followed by stage 310.

Another inspection recipe can be defined if, for example, only a part of the allowable changes in the optical characteristics of the wafer (or of the coating material) were "covered" by the previously defined inspection recipes.

Stage 350 may include determining to define another inspection recipe in order to comply with known manufacturing change processes (e.g. optical liquids reflection degradation, and so forth).

Figure 4:
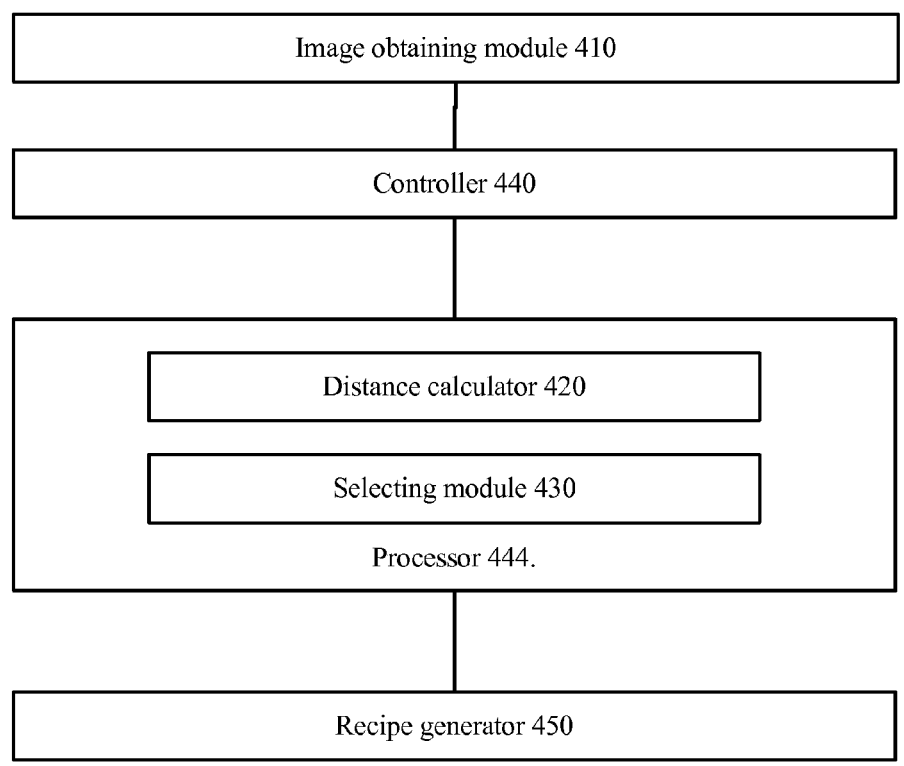
FIG. 4 illustrates an inspection system according to an embodiment of the invention.

FIG. 4 illustrates an inspection system 400, according to an embodiment of the invention.

The inspection system 400 includes:
(i) an image obtaining module 410 for obtaining an image of a structural element of the semiconductor device;
(ii) a distance calculator 420 for calculating multiple types of distances between the image of the structural element and each of a plurality of reference images obtained by applying a plurality of inspection recipes;
(iii) a selecting module 430 for automatically selecting at least one selected inspection recipe out of the plurality of inspection recipes based on values of the multiple types of distances; and
(iv) a controller 440 for controlling the image obtaining module to apply each of the at least one selected inspection recipe.

The inspection system 400 can execute methods 100 and 200. In order to execute method 105 the inspection system 400 it should include recipe generator 450—as illustrated in FIG. 4. It is noted that the inspection system 400 may receive the recipes from another device or system and that the recipe generator 450 can be separate from the inspection system.

The distance calculator 420 and the selecting module 430 can be a part of processor 444.

The distance calculator 420 may be adapted to calculate multiple types of distances, a majority of types of distances or three or more types of distances out of the following: (i) a difference between gray level histograms, (ii) a rectilinear (L1) distance, (iii) Euclidian (L2) length, (iv) Chi-square distance, (v) Bhattacharyya distance, (vi) Wasserstein metric, (vii) Swain metric, and (viii) normalized correlation.

The distance calculator 420 may be adapted to generate a match value for each reference image based on values of the multiple types of distances between the image of the structural element and the reference image; and selecting each inspection recipe associated with a reference image that has a match value within an allowable match value range.

The selecting module 430 may be adapted to select multiple selected inspection recipes.

The distance calculator 420 may be adapted to change the type of distances to be calculated based on evaluation results obtained by applying the at least one selected inspection recipe.

The image obtaining module 410 can include one or more cameras, optics, and one or more sensors, image grabber (not shown) and an image processor. The image obtaining module 410 can be set into different states in response to information that is stored in different inspection recipes. The different states may differ by their optical parameters (e.g. illumination, focal length), physical parameters (e.g. distance from wafer, exposure time, chemical material used), and so forth.

Either one or methods 100, 200 and 300 can be executed by a processor (such as processor 444) that executed instructions. The instructions can be stored in non-transient computer readable medium such as a disk, a tape, a diskette, and the like.

For example, the computer program product may include a non-transient computer readable medium that stores instructions for: obtaining an image of a structural element of the semiconductor device; calculating multiple types of distances between the image of the structural element and each of a plurality of reference images obtained by applying a plurality of inspection recipes; and automatically selecting at least one selected inspection recipe out of the plurality of inspection recipes based on values of the multiple types of distances.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A method for selecting an inspection recipe, the method comprises:
    obtaining an image of a structural element of the semiconductor device;
    calculating, by a processor, multiple types of distances between an image of the structural element and each of a plurality of reference images obtained by applying a plurality of inspection recipes; wherein the multiple types of distances are calculated by using different algorithms;
    wherein a calculation of the multiple types of distances by the distance calculator comprises calculating at least five distances out of a group consisting of: (i) a difference between gray level histograms, (ii) a rectilinear (LI) distance, (iii) Euclidian (L2) length, (iv) Chi-square distance, (v) Bhattacharyya distance, (vi) Wasserstein metric, (vii) Swain metric, and (viii) normalized correlation;
    wherein different inspection recipes of the plurality of inspection recipes are optimized for different conditions of the semiconductor device; wherein each reference image is associated with an inspection recipe before the obtaining of the image of the structural element; and
    automatically selecting, by the processor, at least one selected inspection recipe out of the plurality of inspection recipes based on values of the multiple types of distances.

2. The method according to claim 1, wherein the calculating, by the processor, of the multiple types of distances comprises calculating, by the processor, each one out of (i) a difference between gray level histograms, (ii) a rectilinear (L1) distance, (iii) Euclidian (L2) length, (iv) Chi-square distance, (v) Bhattacharyya distance, (vi) Wasserstein metric, (vii) Swain metric, and (viii) normalized correlation.

3. The method according to claim 1, comprising generating, by the processor, a match value for each reference image based on values of the multiple types of distances between the image of the structural element and the reference image; and selecting each inspection recipe associated with a reference image that has a match value within an allowable match value range.

4. The method according to claim 1, comprising selecting, by the processor, multiple selected inspection recipes.

5. The method according to claim 1, comprising changing, by the processor, the type of distances to be calculated based on evaluation results obtained by applying the at least one selected inspection recipe.

6. The method according to claim 1, wherein the structural elements are coated by a coating material that changes an optical property over time, wherein the plurality of inspection recipes differ from each other by a value of optical property of the coating material they are tuned to.

7. The method according to claim 1 wherein the different conditions comprise a global reflection of the semiconductor device.

8. An inspection system, comprising:
    an image obtaining module that is adapted to obtain an image of a structural element of the semiconductor device; a processor that comprises:
    a distance calculator that is adapted to calculate multiple types of distances between the image of the structural element and each of a plurality of reference images; wherein the multiple types of distances are calculated by using different algorithms;
    wherein a calculation of the multiple types of distances by the distance calculator comprises calculating at least five distances out of a group consisting of: (i) a difference between gray level histograms, (ii) a rectilinear (LI) distance, (iii) Euclidian (L2) length, (iv) Chi-square distance, (v) Bhattacharyya distance, (vi) Wasserstein metric, (vii) Swain metric, and (viii) normalized correlation;
    wherein the plurality of reference images are obtained by applying a plurality of inspection recipes; wherein different inspection recipes of the plurality of inspection recipes are optimized for different conditions of the semiconductor device; wherein each reference image is associated with an inspection recipe before the obtaining of the image of the structural element; and
    a selecting module that is adapted to automatically select at least one selected inspection recipe out of the plurality of inspection recipes based on values of the multiple types of distances; and a controller that is adapted to control the image obtaining module to apply each of the at least one selected inspection recipe.

9. The system according to claim 8, wherein a calculation of the multiple types of distances by the distance calculator comprises calculating (i) a difference between gray level histograms, (ii) a rectilinear (L1) distance, (iii) Euclidian (L2) length, (iv) Chi-square distance, (v) Bhattacharyya distance, (vi) Wasserstein metric, (vii) Swain metric, and (viii) normalized correlation.

10. The system according to claim 8, wherein the distance calculator is adapted to generate a match value for each reference image based on values of the multiple types of distances between the image of the structural element and the reference image; and selecting each inspection recipe associated with a reference image that has a match value within an allowable match value range.

11. The system according to claim 8, wherein the selecting module is adapted to select multiple selected inspection recipes.

12. The system according to claim 8, wherein the distance calculator is adapted to change the type of distances to be calculated based on evaluation results obtained by applying the at least one selected inspection recipe.

13. The system according to claim 8, wherein the structural elements are coated by a coating material that changes an optical property over time, wherein the plurality of inspection recipes differ from each other by a value of optical property of the coating material they are tuned to.

14. A computer program product comprising a nontransient computer readable medium that stores instructions that cause a processor to execute a method that comprises:
   obtaining an image of a structural element of the semiconductor device;
   calculating multiple types of distances between an image of the structural element and each of a plurality of reference images obtained by applying a plurality of inspection recipes;
   wherein the multiple types of distances are calculated by using different algorithms;
   wherein a calculation of the multiple types of distances comprises calculating at least five distances out of a group consisting of: (i) a difference between gray level histograms, (ii) a rectilinear (LI) distance, (iii) Euclidian (L2) length, (iv) Chi-square distance, (v) Bhattacharyya distance, (vi) Wasserstein metric, (vii) Swain metric, and (viii) normalized correlation;
   wherein different inspection recipes of the plurality of inspection recipes are optimized for different conditions of the semiconductor device;
   wherein each reference image is associated with an inspection recipe before the obtaining of the image of the structural element; and automatically selecting at least one selected inspection recipe out of the plurality of inspection recipes based on values of the multiple types of distances.

15. The computer program product according to claim 14, wherein the calculating of the multiple types of distances comprises calculating each type of distance out of: (i) a difference between gray level histograms, (ii) a rectilinear (L1) distance, (iii) Euclidian (L2) length, (iv) Chi-square distance, (v) Bhattacharyya distance, (vi) Wasserstein metric, (vii) Swain metric, and (viii) normalized correlation.

16. The computer program product according to claim 14, further storing instructions that cause the processor to execute a method that comprises generating a match value for each reference image based on values of the multiple types of distances between the image of the structural element and the reference image; and selecting each inspection recipe associated with a reference image that has a match value within an allowable match value range.

17. The computer program product according to claim 14, further storing instructions that cause the processor to execute a method that comprises selecting multiple selected inspection recipes.

18. The computer program product according to claim 14, further storing instructions that cause the processor to execute a method that comprises changing the type of distances to be calculated based on evaluation results obtained by applying the at least one selected inspection recipe.

19. The computer program product according to claim 14, wherein the structural elements are coated by a coating material that changes an optical property over time, wherein the plurality of inspection recipes differ from each other by a value of optical property of the coating material they are tuned to.

* * * * *